United States Patent
Ito et al.

(10) Patent No.: US 9,296,947 B2
(45) Date of Patent: Mar. 29, 2016

(54) PLASMA ETCHING GAS AND PLASMA ETCHING METHOD

(75) Inventors: Azumi Ito, Tokyo (JP); Atsuyo Watanabe, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 60 days.

(21) Appl. No.: 14/008,354

(22) PCT Filed: Mar. 27, 2012

(86) PCT No.: PCT/JP2012/057921
§ 371 (c)(1),
(2), (4) Date: Apr. 23, 2014

(87) PCT Pub. No.: WO2012/133401
PCT Pub. Date: Oct. 4, 2012

(65) Prior Publication Data
US 2014/0306146 A1      Oct. 16, 2014

(30) Foreign Application Priority Data
Mar. 29, 2011 (JP) ................................ 2011-072192

(51) Int. Cl.
| | |
|---|---|
| *H01L 21/3065* | (2006.01) |
| *C09K 13/00* | (2006.01) |
| *C09K 13/08* | (2006.01) |
| *H01L 21/3213* | (2006.01) |
| *H01L 21/311* | (2006.01) |
| *C07C 21/18* | (2006.01) |

(52) U.S. Cl.
CPC ................. *C09K 13/00* (2013.01); *C07C 21/18* (2013.01); *C09K 13/08* (2013.01); *H01L 21/3065* (2013.01); *H01L 21/31116* (2013.01); *H01L 21/32136* (2013.01); *H01L 21/32137* (2013.01)

(58) Field of Classification Search
CPC .. C09K 13/00; C09K 13/08; H01L 21/31116; H01L 21/32136; H01L 21/32137
See application file for complete search history.

(56) References Cited

U.S. PATENT DOCUMENTS

| | | |
|---|---|---|
| 4,529,476 A | 7/1985 | Kawamoto et al. |
| 2001/0005634 A1 | 6/2001 | Kajiwara |
| 2011/0068086 A1 | 3/2011 | Suzuki et al. |

FOREIGN PATENT DOCUMENTS

| | | |
|---|---|---|
| JP | 60-115232 A | 6/1985 |
| JP | 04-170026 A | 6/1992 |
| JP | 2001-250817 A | 9/2001 |
| JP | 2002-016050 A | 1/2002 |
| JP | 2006-514783 A | 5/2006 |
| JP | 2011-044740 A | 3/2011 |
| WO | 2004/034445 A2 | 4/2004 |
| WO | 2009/123038 A1 | 10/2009 |

OTHER PUBLICATIONS

S.J. Moss and K.R. Jennings, "Relative rate constants for the reaction of ground-state oxygen atoms with partly fluorinated propylenes and butenes", Trans. Faraday Soc., vol. 65, year 1969, pp. 415-423.*
International Search Report dated Jun. 19, 2012, corresponding application No. PCT/JP2012/057921.

\* cited by examiner

*Primary Examiner* — Jiong-Ping Lu
(74) *Attorney, Agent, or Firm* — Westerman, Hattori, Daniels & Adrian, LLP

(57) ABSTRACT

The present invention is an etching gas comprising an unsaturated fluorohydrocarbon represented by $C_xH_yF_z$ (wherein x=3, 4, or 5, y+z≤2x, and y>z) and a method comprising selectively etching a silicon nitride film relative to a silicon oxide film or a silicon film using the etching gas. According to the present invention, a silicon nitride film stacked on a silicon oxide film or a silicon film can be highly selectively etched.

16 Claims, No Drawings

PLASMA ETCHING GAS AND PLASMA ETCHING METHOD

TECHNICAL FIELD

The invention relates to a plasma etching gas that is used to selectively etch a silicon nitride film relative to a silicon oxide film or a silicon film when etching a silicon nitride film that covers a silicon oxide film or a silicon film formed on a processing target, and a plasma etching method that utilizes the plasma etching gas.

BACKGROUND ART

A saturated fluorohydrocarbon gas having 3 to 5 carbon atoms may be used as an etching gas (see Patent Documents 1 to 3).

For example, Patent Document 1 discloses a saturated fluorohydrocarbon represented by $C_xH_yF_z$ (wherein x is 3, 4, or 5, and y and z are independently a positive integer, provided that y>z is satisfied) as a gas that is used to selectively etch a silicon nitride film when etching a silicon nitride film that covers a silicon oxide film. In the examples of Patent Document 1, only a silicon nitride film is selectively etched at a rate of 64 nm/min (selectivity ratio: infinity) using 2,2-difluoro-n-butane without etching a silicon oxide film.

Patent Document 2 considers that $C_3H_5F_3$ gas (i.e., one of the saturated fluorohydrocarbons disclosed in Patent Document 1) may be used as an etching gas that achieves a high selectivity ratio (see paragraph 0106). This is because a reaction product is deposited on a mask, and the etching target area is etched.

Patent Document 3 discloses that $C_3H_7F$ and $C_3H_6F_2$ function as a protective film-forming substance during etching when used in combination with another etching gas such as $C_4F_6$ gas or oxygen.

Patent Document 4 discloses that a contact hole having a high aspect ratio can be formed by selectively etching a silicon oxide film, a silicon nitride film, or the like relative to a resist or silicon using a dry etching gas that includes an unsaturated perfluorocarbon (see paragraph 0004).

Several etching techniques that selectively etch a silicon nitride film or the like relative to a silicon oxide film, a silicon film, or the like have been proposed as described above.

However, development of a technique that can more selectively etch a silicon nitride film relative to a silicon oxide film, a silicon film, or the like without damaging another film (particularly a silicon film or a silicon oxide film) has been desired along with the recent development of semiconductor production technology.

RELATED-ART DOCUMENT

Patent Document

Patent Document 1: WO2009/123038 (US2011/068086)
Patent Document 2: JP-A-2001-250817 (US2001/005634)
Patent Document 3: JP-T-2006-514783 (WO2004/034445)
Patent Document 4: JP-A-2002-016050

SUMMARY OF THE INVENTION

Technical Problem

The invention was conceived in view of the above situation. An object of the invention is to provide a plasma etching gas that is used to selectively etch a silicon nitride film relative to a silicon oxide film or a silicon film without damaging a silicon oxide film or a silicon film when etching a silicon nitride film that covers a silicon oxide film or a silicon film formed on the processing target, and a plasma etching method that utilizes the plasma etching gas.

Solution to Problem

An etching technique that does not use argon that becomes a high-energy ion species in plasma has attracted attention as an etching technique that selectively etches a silicon nitride film from the viewpoint of preventing damage to another film (particularly a silicon film).

The inventors of the invention attempted to selectively etch a silicon nitride film relative to a silicon oxide film and a silicon film in the absence of argon using 2,2-difluoro-n-butane disclosed in Patent Document 1 as an etching gas. However, it was found that only a selectivity ratio of about 4 can be obtained relative to a silicon oxide film and a silicon film.

The inventors conducted further extensive studies in order to find an etching gas that can be used to selectively etch a silicon nitride film, and found that high etching selectivity relative to both a silicon oxide film and a silicon film can be achieved by utilizing an unsaturated fluorohydrocarbon represented by $C_xH_yF_z$ (wherein x=3, 4, or 5, y+z≤2x, and y>z) as the etching gas. This finding has led to the completion of the invention.

Several aspects of the invention provide the following etching gas (see (a) and (b)) and etching method (see (c)).
(a) An etching gas including an unsaturated fluorohydrocarbon represented by $C_xH_yF_z$ (wherein x=3, 4, or 5, y+z≤2x, and y>z).
(b) The etching gas according to (a), further including oxygen gas and/or nitrogen gas.
(c) A method including selectively etching a silicon nitride film relative to a silicon oxide film or a silicon film using the etching gas according to (1) or (2).

Advantageous Effects of the Invention

The aspect of the invention provides an etching gas including an unsaturated fluorohydrocarbon represented by $C_xH_yF_z$ (wherein x=3, 4, or 5, y+z≤2x, and y>z). A silicon nitride film can be selectively etched relative to a silicon oxide film or a silicon film using the etching gas according to the aspect of the invention.

DESCRIPTION OF EMBODIMENTS

The term "etching" used herein refers to a technique that etches a processing target used to produce a semiconductor device or the like to form a highly integrated fine pattern. More specifically, the term "etching" used herein refers to a technique that causes a glow discharge by applying a high-frequency electric field to a process gas (i.e., the unsaturated fluorohydrocarbon gas represented by the above formula) to decompose the gaseous compound into chemically active ions, electrons, and radicals, and implements etching by utilizing chemical reactions with the ions, electrons, and radicals.

The term "silicon oxide film" used herein refers to a film that includes silicon oxide, and is formed by thermal oxidation of silicon, or a CVD method that utilizes $SiH_4$ and $O_2$ as a raw material gas, for example.

The term "silicon film" used herein refers to a film that substantially includes only silicon, such as single-crystal silicon, polycrystalline silicon, and amorphous silicon.

The term "silicon nitride film" used herein refers to a film that includes a silicon nitride represented by $Si_aN_b$ (a and b>0), and is formed by a low-pressure CVD method that is performed at about 700° C., and utilizes $SiH_2Cl_2$ and $NH_3$ as a raw material gas, for example.

The embodiments of the invention are described in detail below.

An etching gas according to one embodiment of the invention includes an unsaturated fluorohydrocarbon represented by $C_xH_yF_z$ (wherein x=3, 4, or 5, y+z≤2x, and y>z) (hereinafter may be referred to as "unsaturated fluorohydrocarbon A").

The unsaturated fluorohydrocarbon A may have a linear structure, may have a branched structure, or may have a cyclic structure.

Specific examples of the unsaturated fluorohydrocarbon A include the following compounds.

Unsaturated fluorohydrocarbons represented by $C_3H_5F$: 3-fluoropropene, 2-fluoro-1-propene, (Z)-1-fluoro-1-propene, and (E)-1-fluoro-1-propene Unsaturated fluorohydrocarbons represented by $C_3H_4F_2$: 3,3-difluoro-1-propene, 1,1-difluoro-1-propene, and 1,2-difluoro-1-propene Unsaturated fluorohydrocarbons represented by $C_3H_3F$: propargyl fluoride, fluoroallene, 3-fluoro-1-cyclopropene, 1-fluoro-1-cyclopropene, and 1-fluoro-1-propyne Unsaturated fluorohydrocarbons represented by $C_4H_7F$: 2-methyl-3-fluoro-1-propene, (E)-1-fluoro-2-butene, 3-fluoro-1-butene, (E)-2-fluoro-2-butene, (Z)-2-fluoro-2-butene, cyclopropylmethyl fluoride, and 4-fluoro-1-butene Unsaturated fluorohydrocarbons represented by $C_4H_6F_2$: 1,4-difluoro-2-butene, 1,1-difluoro-2-methylpropene, (Z)-1,2-difluoro-2-butene, 3,3-difluoro-1-butene, and 2-methyl-3,3-difluoro-1-propene Unsaturated fluorohydrocarbons represented by $C_4H_5F_3$: 3,3,3-trifluoro-2-methyl-1-propene, 4,4,4-trifluoro-1-butene, and 1,1,1-trifluoro-2-butene Unsaturated fluorohydrocarbons represented by $C_4H_5F$: 2-fluoro-1,3-butadiene, 2-fluoro-1-methylenecyclopropane, 3-fluorocyclobutene, 3-fluoro-1-butyne, (E)-1-fluoro-1,3-butadiene, (Z)-1-fluoro-1,3-butadiene, 4-fluoro-1-butyne, and 1-fluoro-2-butyne Unsaturated fluorohydrocarbons represented by $C_4H_4F_2$: 1,1-difluoro-1,3-butadiene, 2,3-difluoro-1,3-butadiene, 1,2-difluoro-1-cyclobutene, 3,3-difluorocyclobutene, (difluoromethylene)cyclopropane, (1E,3E)-1,4-difluoro-1,3-butadiene, (1E,3Z)-1,4-difluoro-1,3-butadiene, (1Z,3Z)-1,4-difluoro-1,3-butadiene, 1-methylene-2,2-difluorocyclopropane, and 3,4-difluorocyclobutene Unsaturated fluorohydrocarbons represented by $C_4H_3F$: 1-fluorocyclobutadiene and 1-fluoro-1,2,3-butanetriene Unsaturated fluorohydrocarbons represented by $C_5H_9F$: 5-fluoro-1-pentene, (E)-4-fluoro-2-pentene, (Z)-4-fluoro-2-pentene, and 2-fluoro-3-methyl-2-butene Unsaturated fluorohydrocarbons represented by $C_5H_8F_2$: 2-methyl-1,1-difluoro-1-butene Unsaturated fluorohydrocarbons represented by $C_5H_7F_3$: 4,4,4-trifluoro-2-methyl-1-butene, 4,4,4-trifluoro-2-methyl-2-butene, 5,5,5-trifluoro-1-pentene, 3-trifluoromethyl-1-butene, and 1-methyl-1-(trifluoromethyl)cyclopropane Unsaturated fluorohydrocarbons represented by $C_5H_7F$: 5-fluoro-1,3-pentadiene, 2-fluoromethyl-1,3-butadiene, [fluoromethylene]cyclobutane, 1-fluoro-1-cyclopentene, (E)-4-fluoro-1,3-pentadiene, (Z)-4-fluoro-1,3-pentadiene, (E)-5-fluoro-1,3-pentadiene, (Z)-3-fluoro-1,3-pentadiene, 5-fluoro-2-pentyne, 1-fluoro-1,3-pentadiene, 3-fluoro-3-methyl-1-butyne, -fluoro-3-methyl-1,3-butadiene, 5-fluoro-1-pentyne, and 3-fluoro-1-cyclopentene Unsaturated fluorohydrocarbons represented by $C_5H_6F_2$: 3,4-difluorocyclopentene, 3,5-difluorocyclopentene, 1,1-difluoro-2-methyl-3-methylenecyclopropane, 1,1-difluoro-2-ethylidenecyclopropane, 1-methyl-2-(difluoromethylene)cyclopropane, 1,1-difluoro-2-methyl-1,3-butadiene, 1,1-difluoro-3-methyl-1,3-butadiene, 3,3-difluoro-1,4-pentadiene, (z)-2,4-difluoro-1,3-pentadiene, and 1,1-difluoro-2-vinylcyclopropane Unsaturated fluorohydrocarbons represented by $C_5H_5F_3$: 3-(trifluoromethyl)cyclobutene, 2-(trifluoromethyl)-1,3-butadiene, 1,1,3-trifluoro-2-methyl-1,3-butadiene, 1,1,2-trifluoro-1,3-pentadiene, 1,1,2-trifluoro-1,4-pentadiene, (E)-5,5,5-trifluoro-1,3-pentadiene, (Z)-5,5,5-trifluoro-1,3-pentadiene, (1Z,3E)-1,3,5-trifluoro-1,3-pentadiene, and (1E,3E)-1,3,5-trifluoro-1,3-pentadiene Unsaturated fluorohydrocarbons represented by $C_5H_5F$: 5-fluoro-1,3-cyclopentadiene and 5,5-difluoro-1,3-cyclopentadiene Unsaturated fluorohydrocarbons represented by $C_5H_3F$: 1-fluoro-1,3-pentadiyne These unsaturated fluorohydrocarbons A may be used either alone or in combination. It is preferable to use only one type of unsaturated fluorohydrocarbon A in order to more significantly achieve the advantageous effects of the invention.

It is preferable to use 4-fluoro-1-butene, 2-methyl-3-fluoro-1-propene, and 1,1-difluoro-2-methylpropene from the viewpoint of the etching performance, availability, and ease of handling.

Most of the unsaturated fluorohydrocarbons A are known substances, and may be produced (obtained) by a known method.

For example, the unsaturated fluorohydrocarbons A may be produced by the method described in the Journal of the American Chemical Society, 78, 2608 (1956).

A commercially available unsaturated fluorohydrocarbon may also be used either directly or after purification.

The unsaturated fluorohydrocarbon A is introduced into an arbitrary container (e.g., cylinder) in the same manner as a known semiconductor process gas, and is used for plasma etching (described later).

The purity of the unsaturated fluorohydrocarbon A (gas) is preferably 99 vol % or more, more preferably 99.9 vol % or more, and particularly preferably 99.98 vol % or more. When the purity of the unsaturated fluorohydrocarbon A is within the above range, the advantageous effects of the invention are more reliably achieved. If the purity of the unsaturated fluorohydrocarbon A is too low, the purity of gas (i.e., the content of the unsaturated fluorohydrocarbon) inside the gas-filled container may become uneven. Specifically, the purity of gas may significantly differ between the initial stage and a stage when the amount of gas has decreased.

In this case, a large difference in plasma etching performance may occur between the initial stage and a stage when the amount of gas has decreased, and yield may decrease during industrial production. The purity of gas does not become uneven inside the container by increasing the purity of gas (i.e., a difference in plasma etching performance does not occur between the initial stage and a stage when the amount of gas has decreased), so that the gas can be efficiently utilized.

The purity of the unsaturated fluorohydrocarbon A refers to a purity based on volume that is derived from the weight percentage (%) determined by gas chromatography analysis using an internal standard substance method.

An etching gas is normally used as a mixed gas prepared by appropriately mixing oxygen gas, nitrogen gas, and/or an inert gas with the unsaturated fluorohydrocarbon A (gas) (described later).

However, a trace amount of impurities such as air, nitrogen gas contained in production equipment, a solvent used during production, and water derived from hygroscopic salts and alkalis may be present in the unsaturated fluorohydrocarbon A.

When nitrogen gas, oxygen gas, water, or the like is present in the unsaturated fluorohydrocarbon A contained in the container, the mixed gas must be prepared taking account of the amount of such a gas. This is because nitrogen gas, oxygen gas, water, or the like significantly affects the plasma reaction of the unsaturated fluorohydrocarbon A through dissociation in a plasma reactor and production of various free radicals (etching species).

When impurities (e.g., nitrogen gas, oxygen gas, and water) are present in the container that is filled with the unsaturated fluorohydrocarbon A, the composition of the unsaturated fluorohydrocarbon A and impurities discharged from the container may differ between the time immediately after the container is opened and the time when the amount of the unsaturated fluorohydrocarbon A in the container has decreased, and identical etching performance may not be obtained.

Therefore, the total amount of nitrogen gas and oxygen gas included in the unsaturated fluorohydrocarbon A as a residual trace gas is preferably 200 ppm by volume or less, more preferably 150 ppm by volume or less, and particularly preferably 100 ppm by volume or less, based on the total amount of the unsaturated fluorohydrocarbon A (gas). The water content in the unsaturated fluorohydrocarbon A is preferably 30 ppm by weight or less, more preferably 20 ppm by weight or less, and particularly preferably 10 ppm by weight or less.

The total amount of nitrogen gas and oxygen gas refers to the total content (ppm by volume) of nitrogen gas and oxygen gas determined by gas chromatography using the absolute calibration method. Note that the unit "ppm by volume" is equivalent to "ppm by mole". The water content normally refers to a water content (ppm by weight) determined by the Karl Fisher method.

The etching gas according to the embodiments of the invention preferably further includes oxygen gas and/or nitrogen gas in addition to the unsaturated fluorohydrocarbon A (gas). The selectivity ratio can be significantly improved by utilizing oxygen gas and/or nitrogen gas in addition to the unsaturated fluorohydrocarbon A (gas) while preventing an etching stop phenomenon that is considered to occur due to deposition of reaction products at the bottom of a hole.

The volume ratio of oxygen gas, nitrogen gas, or oxygen gas and nitrogen gas to the unsaturated fluorohydrocarbon A (gas) is preferably 0.1 to 150, and more preferably 1 to 15.

The feed rate of each process gas may be proportional to the amount of each gas. For example, the unsaturated fluorohydrocarbon (gas) is fed at a rate of $8.45 \times 10^{-3}$ to $1.69 \times 10^{-1}$ Pa·m$^3$/sec (5 to 100 sccm), and oxygen gas is fed at a rate of $8.45 \times 10^{-3}$ to $8.45 \times 10^{-1}$ Pa·m$^3$/sec (5 to 1500 sccm).

The pressure inside the chamber into which the etching gas has been introduced is normally 0.1 to 100 Pa, and preferably 1 to 10 Pa.

A glow discharge is caused by applying a high-frequency electric field to the unsaturated fluorohydrocarbon A (gas) (reactive plasma gas) contained in the chamber using a plasma generator to generate plasma.

Examples of the plasma generator include a helicon wave-type plasma generator, a high-frequency induction-type plasma generator, a parallel plate-type plasma generator, a magnetron-type plasma generator, a microwave-type plasma generator, and the like. It is preferable to use a helicon wave-type plasma generator, a high-frequency induction-type plasma generator, or a microwave-type plasma generator since high-density plasma can be easily generated.

The plasma density is not particularly limited. It is preferable to etch the processing target in a high-density plasma atmosphere having a plasma density of $10^{11}$ ions/cm$^3$ or more, and more preferably $10^{12}$ to $10^{13}$ ions/cm$^3$, in order to more easily achieve the advantageous effects of the invention.

The temperature of the processing target substrate that is reached during etching is not particularly limited, but is preferably −50 to +300° C., more preferably −20 to +100° C., and still more preferably 0 to 50° C. The temperature of the substrate may or may not be controlled by cooling or the like.

A plasma etching method according to one embodiment of the invention includes generating plasma in a chamber using an etching gas that includes an unsaturated fluorohydrocarbon, and etching a given area of a processing target placed inside the chamber. The plasma etching method according to one embodiment of the invention preferably selectively subjects a silicon nitride film to plasma etching, and more preferably selectively subjects a silicon nitride film to plasma etching relative to a silicon oxide film and/or a silicon film.

The selectivity ratio of a silicon nitride film to a silicon oxide film and/or a silicon film can be increased to 10 or more (infinity in many cases) by etching a silicon nitride film and/or a silicon film under the above etching conditions, and a significantly high selectivity ratio can be achieved as compared with a known method while preventing an etching stop phenomenon due to deposited products.

A silicon nitride film can be selectively etched relative to a silicon oxide film or a silicon film by utilizing the etching gas according to the embodiments of the invention. More specifically, a silicon nitride film stacked on a silicon oxide film or a silicon film can be highly selectively etched by utilizing the etching gas according to the embodiments of the invention.

EXAMPLES

The invention is further described below by way of examples. Note that the invention is not limited to the following examples. The units "parts" and "%" respectively refer to "parts by weight" and "wt %" unless otherwise indicated.

(1) Production Example 1

Production of 4-fluoro-1-butene

A four-necked flask (1l) was charged with 3-buten-1-ol (72 g), dry tetrahydrofuran (400 ml), and methanesulfonyl chloride (126 g), and the mixture was subjected to a nitrogen stream. After sufficiently cooling the flask with ice water, triethylamine (111 g) was slowly added dropwise to the flask from a dropping funnel After the dropwise addition, the mixture was stirred for about 30 minutes while cooling the flask with ice water, and then stirred at room temperature for about 4 hours. After completion of the reaction, 100 ml of tetrahydrofuran was added to the mixture, and salts (triethylamine hydrochloride) produced by the reaction were filtered off Most of the tetrahydrofuran was evaporated from the filtrate using an evaporator. After the addition of 200 ml of diethyl ether to the residue, the mixture was sequentially washed with 5% hydrochloric acid, a saturated sodium bicarbonate aqueous solution, and a saturated sodium chloride solution, and dried over anhydrous magnesium sulfate, and magnesium sulfate was filtered off Diethyl ether was evaporated from the filtrate using an evaporator to obtain 126 g of 4-methanesulfonyloxy-1-butene (hereinafter referred to as "mesylate") as a yellowish brown oil (yield: 84%).

A four-necked flask equipped with a condenser (provided with a simple distillation apparatus) and a three-one motor was charged with spray-dried potassium fluoride and diethylene glycol, and the mixture was heated to 90° C. with stirring under a nitrogen stream. The mesylate was added dropwise to the mixture using a dropping funnel. The mixture was stirred at 90° C. for 6 hours, and cooled to room temperature. The mixture was then heated to 60° C. with stirring under a reduced pressure of $1.33 \times 10^4$ to $1.4 \times 10^4$ Pa (100 to 105 mmHg). The resulting reaction mixture was purified by vacuum distillation to obtain 122 g of the target 4-fluoro-1-butene. The purity of the resulting 4-fluoro-1-butene was 99.5%.

(2) Production Example 2

Production of 2-methyl-3-fluoropropene

A glass reactor (500 ml) equipped with a Dimroth condenser (in which a refrigerant (0° C.) was circulated) was charged with 75.7 g (0.24 mol) of t-butylammonium fluoride trihydrate and 120 ml of dry dimethyl sulfoxide to dissolve t-butylammonium fluoride trihydrate. After the addition of 18.1 g (0.2 mol) of methallyl chloride to the solution, the mixture was stirred for 10 hours in a nitrogen atmosphere. The reaction mixture was then distilled to obtain 10.8 g of the target 2-methyl-3-fluoropropene (yield: 73%). The purity of the resulting 2-methyl-3-fluoropropene was 99.8%.

(3) Production Example 3

Production of 1,1-difluoro-2-methylpropene

A three-necked flask (reactor) (100 ml) equipped with a Dimroth condenser and a dropping funnel was provided. A glass tube was attached to the upper part of the Dimroth condenser, and a pear-shaped flask immersed in a dry ice/ethanol bath was attached through a branch tube. Nitrogen was introduced from the branch tube, and a refrigerant (15° C.) was circulated through the Dimroth condenser.

The reactor was charged with 4.36 g (0.115 mol) of $LiAlH_4$. After the addition of 50 ml of dry tetrahydrofuran, the mixture was stirred at room temperature. 12.36 g (0.1 mol) of 3-chloro-3,3-difluoro-2-methylpropene was slowly added dropwise to the mixture over 1 hour using a dropping funnel. After the dropwise addition, the reactor was heated to 60° C., and the mixture was reacted at 60° C. for 4 hours. After increasing the temperature of the refrigerant that was circulated through the Dimroth condenser to 20° C., the reaction mixture was stirred at 65° C. for 1 hour.

The reaction mixture was then distilled to obtain 6.35 g of the target 1,1-difluoro-2-methylpropene (yield: 69%). The purity of the resulting 1,1-difluoro-2-methylpropene was 99.5%.

Examples 1 to 3 and Comparative Examples 1 and 2

A wafer (1) on which a silicon nitride film ($Si_3N_4$ (referred to as "SiN" in Table 1)) was formed, a wafer (2) on which a silicon oxide film ($SiO_2$ (referred to as "SiO" in Table 1)) was formed, and a wafer (3) on which a polycrystalline silicon film (poly-Si (referred to as "Si" in Table 1)) was formed, were placed in an etching chamber of a parallel plate-type plasma etching apparatus. After evacuating the system, oxygen gas was introduced into the etching chamber at a rate of $2.03 \times 10^{-1}$ Pa·m$^3$/sec (120 sccm), and each of the unsaturated fluorohydrocarbon gases obtained in Production Examples 1 to 3 was introduced into the etching chamber at a flow rate of $1.69 \times 10^{-2}$ to $1.69 \times 10^{-1}$ Pa·m$^3$/sec (10 to 100 sccm). The pressure inside the system was maintained at 6.7 Pa, and 200 W (60 MHz) and 100 W (2 MHz) were respectively applied to the upper electrode and the lower electrode to effect plasma etching. The etching rate of the silicon nitride film formed on the wafer (1), the etching rate of the silicon oxide film formed on the wafer (2), and the etching rate of the silicon film formed on the wafer (3) were measured, and the selectivity ratio was calculated from the ratio of the etching rate of the silicon nitride film to the etching rate of the silicon oxide film or the silicon film based on the measurement results.

Table 1 shows the etching rate measurement results for the silicon nitride film, the silicon oxide film, and the silicon film, and the selectivity ratio calculation results on an etching gas flow rate basis. In Table 1, a case where etching did not proceed, and a fluorocarbon film derived from the etching gas was deposited is indicated by "Deposition".

TABLE 1

| | | Example 1 | | | Example 2 | | | Example 3 | | | Comparative Example 1 | | | Comparative Example 2 | | |
|---|---|---|---|---|---|---|---|---|---|---|---|---|---|---|---|---|
| Gas | | 4-Fluoro-1-butene | | | 2-Methyl-3-fluoro-1-propene | | | 1,1-Difluoro-2-methylpropene | | | Fluoromethane | | | 2,2-Difluorobutane | | |
| Film material | | SiN | SiO | Si | SiN | SiO | Si | SiN | SiO | Si | SiN | SiO | Si | SiN | SiO | Si |
| Upper part: etching rate[2] / Lower part: selectivity ratio[3] | Flow rate[1] | | | | | | | | | | | | | | | |
| | 1.7 | 4.8 | 4.3 | 4.9 | 10.5 | 5.9 | 4.4 | 10.4 | 5.1 | 5.8 | | | | | | |
| | | — | 1.1 | 1 | — | 1.8 | 2.4 | — | 2 | 1.8 | | | | | | |
| | 3.8 | 25.5 | 4.8 | 5.6 | 27.8 | 5.9 | 5.8 | 28.7 | 6.3 | 6.9 | 6 | 6.4 | 6.9 | 12.8 | 5.3 | 6.3 |
| | | — | 5.3 | 4.6 | — | 4.7 | 4.8 | — | 4.6 | 4.1 | — | 0.9 | 0.9 | — | 2.4 | 2 |
| | 4.2 | | | | 27 | 6.2 | 5.4 | | | | | | | | | |
| | | | | | — | 4.4 | 5 | | | | | | | | | |
| | 4.7 | | | | 18.2 | 33.5 | Deposition | | | | | | | | | |
| | | | | | — | 0.5 | Infinity | | | | | | | | | |
| | 4.9 | 19.6 | 5 | 5.7 | 16.6 | Deposition | Deposition | | | | | | | | | |
| | | — | 3.9 | 3.4 | — | Infinity | Infinity | | | | | | | | | |
| | 5.1 | 18.3 | 3.1 | 4.2 | Deposition | Deposition | Deposition | 25.3 | 5.2 | 6 | | | | | | |
| | | — | 5.9 | 4.3 | | | | — | 4.9 | 4.2 | | | | | | |

TABLE 1-continued

| Example 1 | | | | Example 2 | | Example 3 | | | Comparative Example 1 | | | Comparative Example 2 | | |
|---|---|---|---|---|---|---|---|---|---|---|---|---|---|---|
| 5.2 | 20.6 | 28.1 | Deposition | | | | | | | | | | | |
| | — | 0.7 | Infinity | | | | | | | | | | | |
| 5.3 | 16.9 | Deposition Infinity | Deposition Infinity | | | | | | | | | | | |
| 5.6 | Deposition | Deposition | Deposition | | | 21.4 | 10.1 | 6.7 | | | | | | |
| | | | | | | — | 2.1 | 3.2 | | | | | | |
| 6.3 | | | | | | 19.6 | Deposition Infinity | Deposition Infinity | | | | | | |
| 6.8 | | | | | | Deposition | Deposition | Deposition | 12.8 | 5.3 | 5.9 | 32.6 | 8 | 7.2 |
| | | | | | | | 2.4 | 2.2 | — | 4.1 | 4.5 | | | |
| 10.1 | | | | | | | | | 12 | 9.1 | 6.2 | 30.8 | 6.9 | 7.4 |
| | | | | | | | 1.3 | 1.9 | — | 4.5 | 4.1 | | | |
| 13.5 | | | | | | | | | 12.4 | 7.2 | 6 | 27.5 | 6.3 | 6.6 |
| | | | | | | | 1.7 | 2.1 | — | 4.3 | 4.2 | | | |
| 16.9 | | | | | | | | | 11.7 | 6.9 | 6.4 | 25.4 | 5.2 | 6.2 |
| | | | | | | | 1.7 | 1.8 | — | 4.9 | 4.1 | | | |

[1] Unit: $\times 10^{-2}$ Pa·m$^3$/sec,
[2] Unit: nm/min,
[3] SiN etching rate/SiO etching rate, or SiN etching rate/Si etching rate As is clear from the etching rate measurement results for the silicon nitride film, the silicon oxide film, and the silicon film shown in Table 1, it was confirmed that the silicon nitride film was selectively etched (i.e., the selectivity ratio was infinity) in Examples 1 to 3 in the absence of argon gas.

The invention claimed is:

1. A method for preparing an etched silicon nitride film, the method comprising: selectively etching a silicon nitride film relative to a silicon oxide film or a silicon film using an etching gas comprising an unsaturated fluorohydrocarbon selected from the group consisting of 4-fluoro-1-butene, 2-methyl-3-fluoro-1-propene, and 1,1-difluoro-2-methylpropene.

2. The method according to claim 1, the etching gas further comprising oxygen gas.

3. The method according to claim 2, wherein a volume ratio of the oxygen gas to the unsaturated fluorohydrocarbon (gas) is 0.1 to 150.

4. The method according to claim 1, the etching gas further comprising nitrogen gas.

5. The method according to claim 4, wherein a volume ratio of the nitrogen gas to the unsaturated fluorohydrocarbon (gas) is 0.1 to 150.

6. The method according to claim 1, the etching gas further comprising oxygen gas and nitrogen gas.

7. The method according to claim 6, wherein a volume ratio of the oxygen gas and the nitrogen gas to the unsaturated fluorohydrocarbon (gas) is 0.1 to 150.

8. The method according to claim 1, wherein the unsaturated fluorohydrocarbon is 4-fluoro-1-butene.

9. The method according to claim 1, wherein the unsaturated fluorohydrocarbon is 2-methyl-3-fluoro-1-propene.

10. The method according to claim 1, wherein the unsaturated fluorohydrocarbon is 1,1-difluoro-2-methylpropene.

11. The method according to claim 1, wherein a water content in the unsaturated fluorohydrocarbon is 30 ppm by weight or less.

12. The method according to claim 1, wherein the unsaturated fluorohydrocarbon is fed at a rate of $8.45 \times 10^{-3}$ to $1.69 \times 10^{-1}$ Pa·m$^3$/sec (5 to 100 sccm).

13. The method according to claim 1, the etching gas further comprises oxygen gas which is fed at a rate of $8.45 \times 10^{-3}$ to $8.45 \times 10^{-1}$ Pa·m$^3$/sec (5 to 1500 sccm).

14. The method according to claim 1, wherein the silicon nitride film is etched with a plasma density of $10^{11}$ ions/cm$^3$ or more.

15. The method according to claim 1, wherein the silicon nitride film is etched with a selectivity ratio of 10 or more, the selectivity ratio being a ratio of the silicon nitride film to the silicon oxide film and/or the silicon film.

16. The method according to claim 1, wherein the silicon nitride film is etched with a selectivity ratio of infinity, the selectivity ratio being a ratio of the silicon nitride film to the silicon oxide film and/or the silicon film.

* * * * *